US00PP11105P

United States Patent [19]

Dümmen

[11] Patent Number: Plant 11,105

[45] Date of Patent: Oct. 19, 1999

[54] POINSETTIA PLANT NAMED 'DUEMAL'

[75] Inventor: Marga Dümmen, Rheinberg, Germany

[73] Assignee: Dümmen Jungpflanzenkulturen, Rheinberg, Germany

[21] Appl. No.: 09/038,773

[22] Filed: Mar. 11, 1998

[51] Int. Cl.[6] ..... A01H 5/00

[52] U.S. Cl. ..... Plt./307

[58] Field of Search ..... Plt./307

*Primary Examiner*—Howard J. Locker
*Assistant Examiner*—Kent L. Bell
*Attorney, Agent, or Firm*—C. A. Whealy

[57] ABSTRACT

A new and distinct variety of Poinsettia plant named 'Duemal', characterized by its dark red flower bracts that are angled upright with respect to stem axis; very dark green leaves; relatively compact and freely branching plant habit; and excellent postproduction longevity.

1 Drawing Sheet

BACKGROUND OF THE INVENTION

The present invention relates to a new and distinct variety of Poinsettia plant, botanically known as *Euphorbia pulcherrima* Willd., and hereinafter referred to by the name 'Duemal'. The new cultivar is being marketed under 'Red Fox Malibu Red'.

The new Poinsettia is a product of a planned breeding program conducted by the inventor in Rheinberg, Germany. The objective of the breeding program was to develop new Poinsettias that are freely branching; flower early; have desirable flower bract and leaf color; and have excellent postproduction longevity.

The new cultivar originated from a cross made by the inventor of the Poinsettia 'Fiscor' (disclosed in U.S. Plant Pat. No. 9,364) as the male or pollen parent with a proprietary Poinsettia selection identified as code number Eup 101 as the female or seed parent. 'Duemal' was discovered and selected in 1995 by the inventor as a single flowering plant within the progeny of the stated cross in a controlled environment in Rheinberg, Germany.

Asexual reproduction of the new Poinsettia by terminal cuttings taken at Rheinberg, Germany, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Duemal'. These characteristics in combination distinguish 'Duemal' as a new and distinct variety:

1. Dark red flower bracts.
2. Flower bracts angled upright with respect to stem axis.
3. Very dark green foliage.
4. Relatively compact and freely branching plant habit.
5. Excellent postproduction longevity.

In side-by-side comparisons conducted by the inventor in Rheinberg, Germany, plants of the new Poinsettia differed from plants of the male parent, 'Fiscor', in the following characteristics:

1. Flower bracts of plants of the new Poinsettia are darker red and more intense in color than flower bracts of plants of 'Fiscor'.

2. Leaves of plants of the new Poinsettia are darker green than leaves of plants of 'Fiscor'.

3. Plants of the new Poinsettia are more freely branching than plants of 'Fiscor'.

4. Plants of the new Poinsettia are more compact than plants of 'Fiscor'.

In side-by-side comparisons conducted by the inventor in Rheinberg, Germany, plants of the new Poinsettia differed from plants of the female parent, Eup 101, in the following characteristics:

1. Flower bracts of plants of the new Poinsettia are darker red and more intense in color than flower bracts of plants of Eup 101.

2. Leaves of plants of the new Poinsettia are darker green and more reddish than leaves of plants of Eup 101.

3. Plants of the new Poinsettia are taller than plants of Eup 101.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. The photograph comprises a top perspective view of a typical plant of 'Duemal' that was pinched and grown in a 15-cm container.

DETAILED BOTANICAL DESCRIPTION

Plants of 'Duemal' have not been observed under all possible environmental conditions. The phenotype may vary somewhat with variations in environment such as temperature, daylength and light intensity, without, however, any variance in genotype. The following observations and measurements describe plants grown in Rheinberg, Germany, under commercial practice in a glass-covered greenhouse with day temperatures about 22° C., night temperatures about 18° C. and light levels about 30 to 40 klux. Plants were grown in 15-cm pots, pinched one time, and flowered under long nyctoperiods.

In the following description, color references are made to The Royal Horticultural Society Colour Chart except where general terms of ordinary dictionary significance are used.

Botanical classification: *Euphorbia pulcherrima* Willd. 'Duemal'.

Parentage:

*Male, or pollen, parent.*—*Euphorbia pulcherrima* Willd. 'Fiscor'.

*Female, or seed, parent.*—Proprietary selection of *Euphorbia pulcherrima* Willd. identified as code number Eup 101.

Propagation:

*Type cutting.*—Terminal cuttings.

*Time to develop roots.*—Summer: About 21 days at 27° C. Winter: About 28 days at 20° C.

*Rooting habit.*—Fine, freely branching.

Plant description:

*Plant form.*—Inverted triangle, top of plant rounded to flat.

*Growth habit.*—Freely branching and upright. Branching is enhanced by removing the shoot apex. Moderate growth rate and moderately vigorous. Suitable for 6 to 16-cm containers.

*Plant height.*—About 25 cm.

*Crop time.*—From unrooted cuttings to a flowering plant in a 15-cm container, about 15 weeks are required.

*Foliage description.*—Quantity of leaves: Usually 65 to 75 per flowering plant. Length: About 13.8 cm. Width: About 10.5 cm. Shape: Hastate to deltoid. Apex: Apiculate. Base: Acute. Margin: Entire. Texture: Velvety, glabrous. Color: Young foliage, upper surface: 147A. Young foliage, lower surface: 147B. Mature foliage, upper surface: Very dark green, close to 131A. Mature foliage, lower surface: 131B/131C. Venation, upper surface: 148A. Venation, lower surface: 148B. Petiole Length: About 4.8 cm. Color: 136A.

Inflorescence Description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions.

*Time to flower.*—About 9 weeks under long nyctoperiod conditions.

*Quantity of inflorescences.*—One per lateral branch, usually about 8 per plant.

*Inflorescence size.*—Diameter: About 30 cm. Height (depth): About 7 cm.

*Flower bracts.*—Orientation: Angled upright. Quantity of flower bracts per inflorescence: About 20 per inflorescence. Length: About 13 cm. Width: About 9.25 cm. Shape: Mostly ovate, occasionally lobed. Apex: Apiculate. Texture: Smooth, satiny. Color: Mature, upper surface: Close to 46A/53A, bract color may fade to 53B. Mature, lower surface: 46C/53B/53C.

*Cyathia.*—Quantity: Usually about 10 to 14 per corymb. Diameter of cyathia cluster: About 3.5 cm. Length: About 1.5 cm. Width: About 5 mm. Color: Immature: 144B. Mature: 144C. Peduncle: Length: About 2 cm. Aspect: Erect. Color: 53A/143A. Stamens: Stamen number: About 10 per cyathium. Anther size: About 1 to 2 mm. Anther shape: Rounded. Anther color: 144B. Pollen color: 10B/10C to 21B. Pistils: Pistil number: 1 to 2 per cyathium. Stigma shape: Trilobate. Stigma color: 20A. Style length: About 3 mm. Style color: 20A. Ovary number: Three. Nectaries: Usually one and sometimes two per cyathium.

Disease resistance: No fungal, bacterial nor viral problems observed on plants grown under commercial conditions.

Postproduction Longevity: Generally plants maintain good substance and bract color for about five to six weeks under interior conditions.

It is claimed:

1. A new and distinct variety of Poinsettia plant named 'Duemal', as illustrated and described.

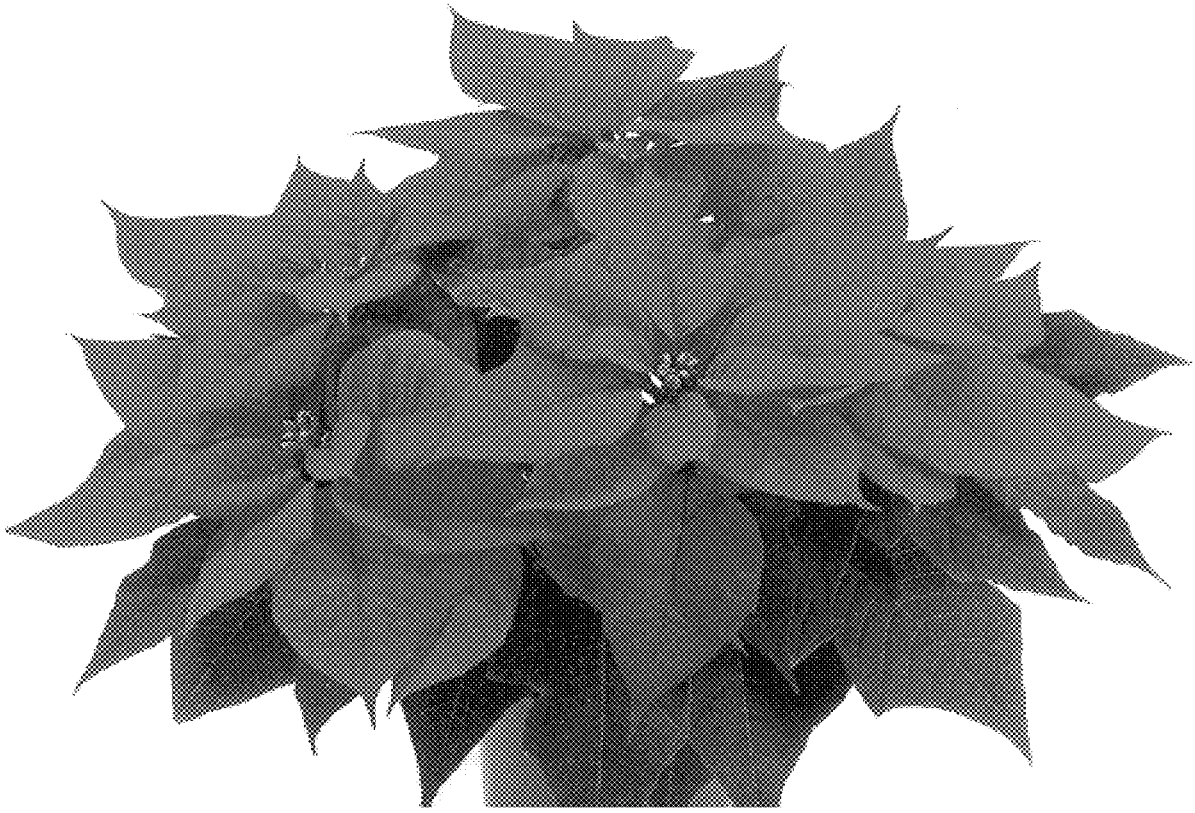

* * * * *